United States Patent [19]

Reinicke et al.

[11] Patent Number: 4,715,852
[45] Date of Patent: Dec. 29, 1987

[54] IMPLANTED MEDICATION INFUSION DEVICE

[75] Inventors: Robert H. Reinicke, Mission Viejo; Lance M. Yamato, Rancho Palos Verdes, both of Calif.

[73] Assignee: Eaton Corporation, Cleveland, Ohio

[21] Appl. No.: 888,585

[22] Filed: Jul. 21, 1986

[51] Int. Cl.$^4$ .............................................. A61M 7/00
[52] U.S. Cl. ........................... 604/131; 128/DIG. 12
[58] Field of Search ............ 604/131, 118, 121, 65–67, 604/326, 280, 283, 28; 128/79, DIG. 12

[56] References Cited

U.S. PATENT DOCUMENTS

| | | | |
|---|---|---|---|
| 4,265,241 | 5/1981 | Portner et al. | 604/131 |
| 4,360,019 | 11/1982 | Portner et al. | 604/131 |
| 4,460,355 | 7/1984 | Layman | 604/121 |
| 4,490,137 | 12/1984 | Moukheibir | 604/28 |
| 4,604,090 | 8/1986 | Reinicke | 604/118 |

Primary Examiner—C. Fred Rosenbaum
Assistant Examiner—Gene B. Kartchner
Attorney, Agent, or Firm—D. A. Rowe; L. G. Vande Zande

[57] ABSTRACT

An implantable positive pressure medication infusion device is provided which is programmable over a wide dynamic range and yet the maximum flow of medication into the body, in the event the inlet valve of the device leaks or fails in the valve open position, is limited to a safe value which is much lower than the maximum programmable infusion rate of the device. An auxiliary flow restrictor is also provided which bypasses the programmable pumping unit and assures a minimum flow of medication into the body in the event of failure of the programmable pumping unit or its electronic drive. An arrangement is also provided for detecting catheter clogging or failure of the programmable pumping unit in either a positive or negative pressure device.

20 Claims, 19 Drawing Figures

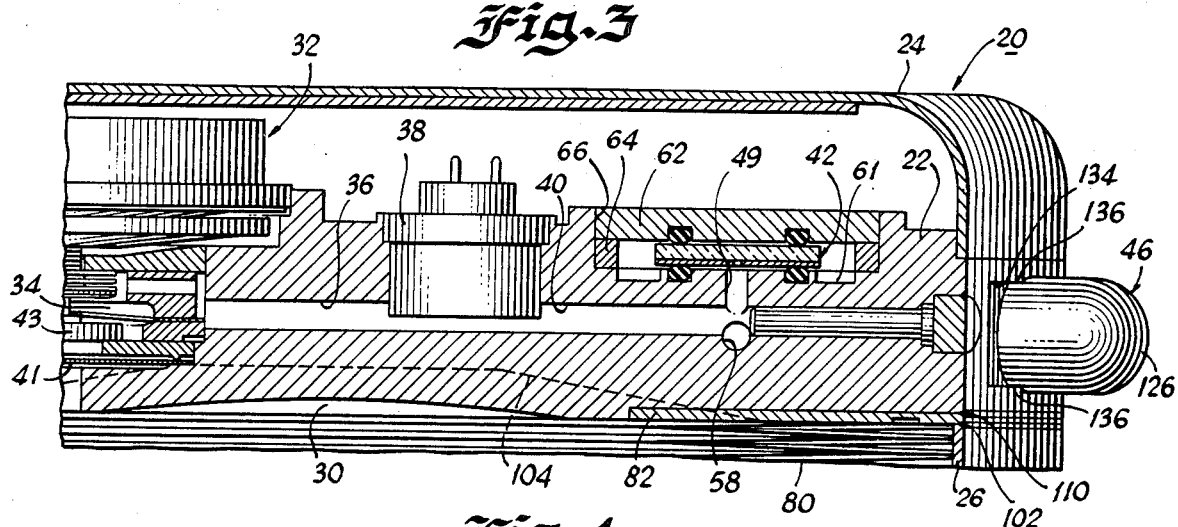
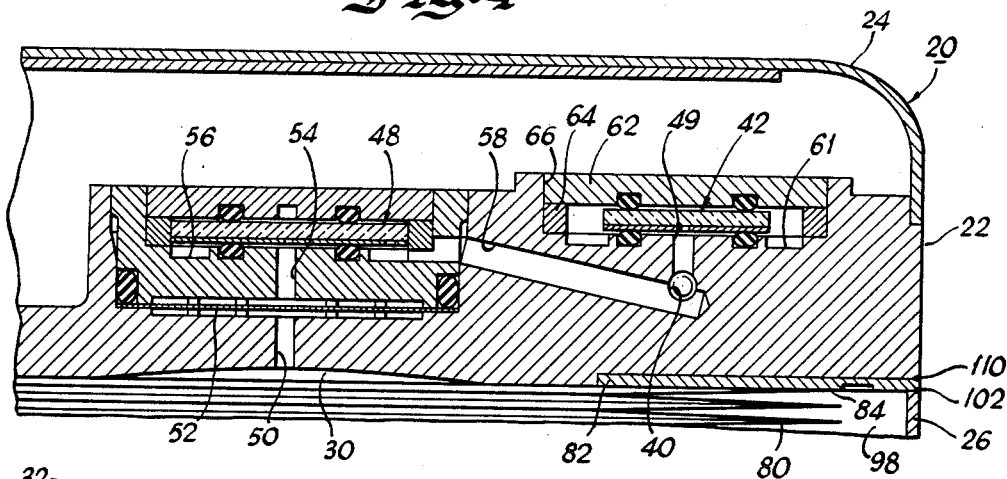
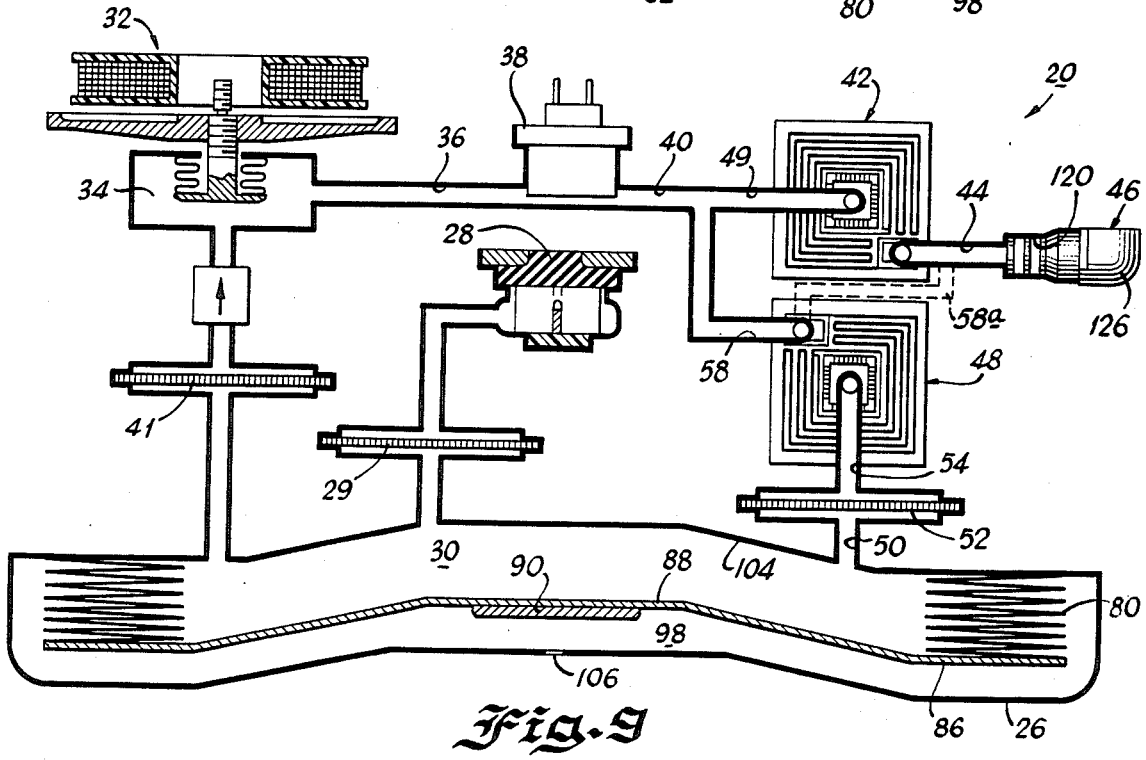

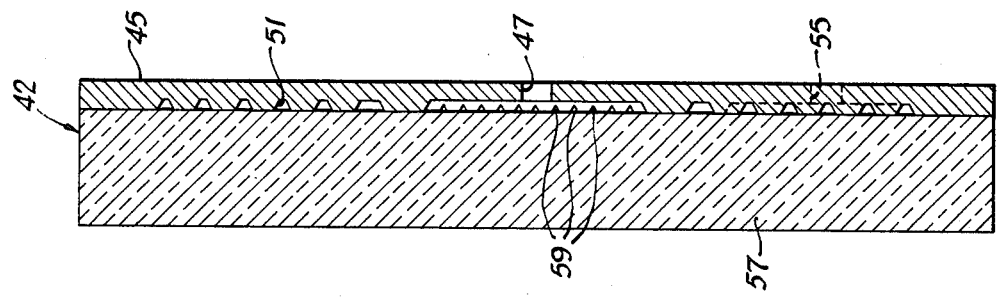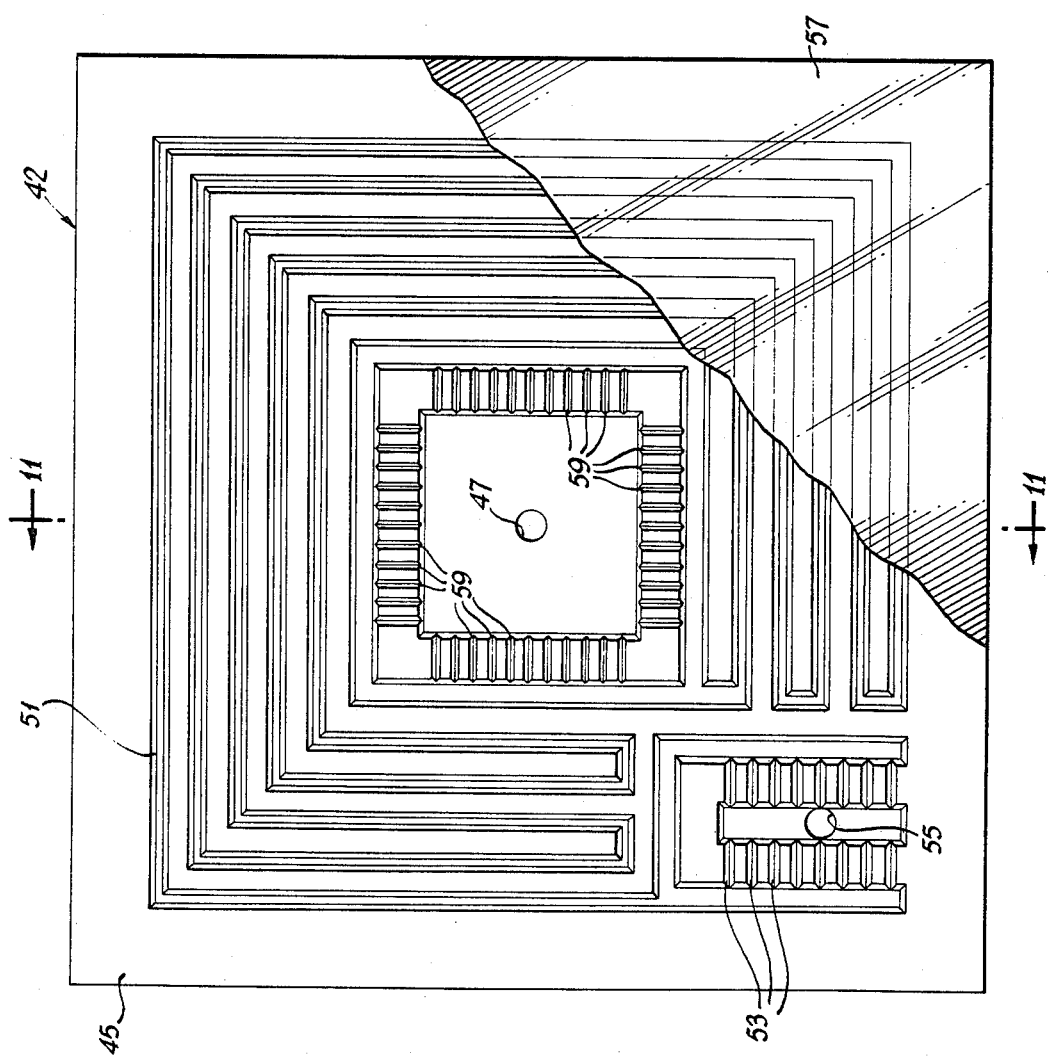

CHANGING INSULIN POTENCY, SINGLE PUMP DESIGN

TIME PERIOD BETWEEN REFILLS
400 U MAX. POTENCY

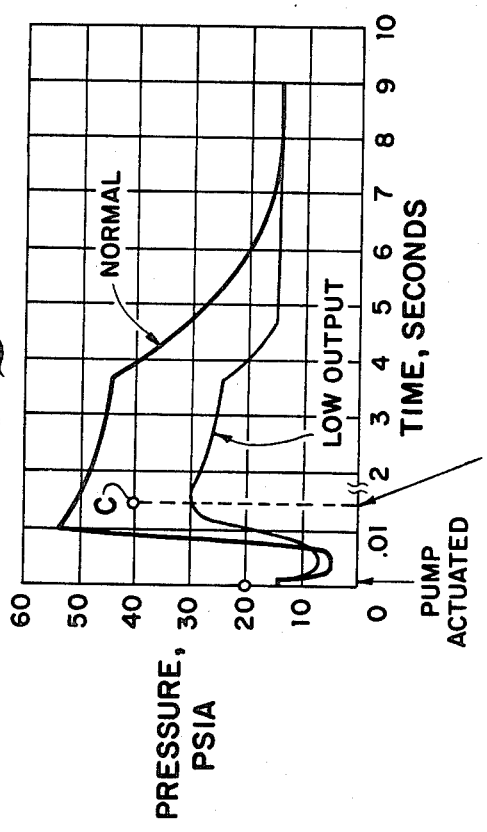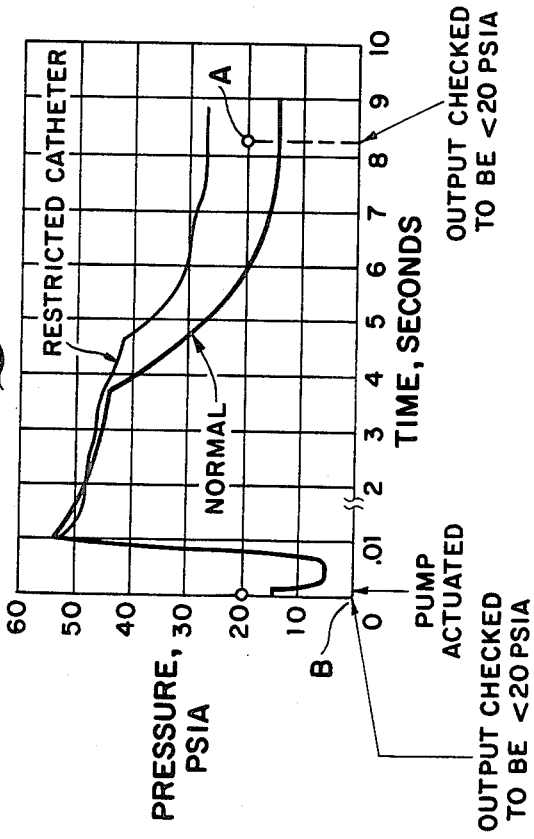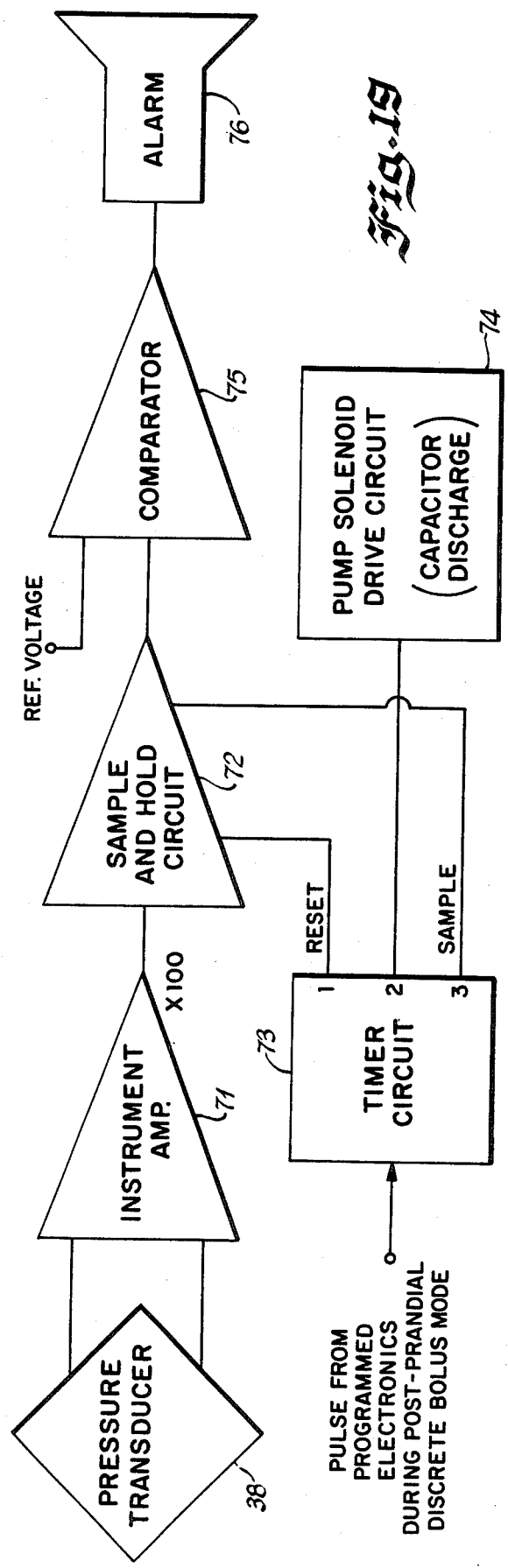

IMPLANTED MEDICATION INFUSION DEVICE

The present invention relates to implantable medication infusion devices, and, more particularly, to implantable medication infusion devices which employ a pulsatile type of pumping unit which may be programmed to provide a variable flow of medication in accordance with the requirements of a particular patient.

Many implantable devices of the prior art have employed such a pulsatile pumping unit to provide a programmable flow of medication, as shown, for example in Summers U.S. Pat. No. 3,527,220; Ellinwood U.S. Pat. No. 3,692,027; Ellinwood U.S. Pat. No. 3,923,060; Thomas et al U.S. Pat. No. 3,963,380; Haerten et al U.S. Pat. No. 4,077,405; Ellinwood U.S. Pat. No. 4,146,029; Moody U.S. Pat. No. 4,152,098; Franetzki et al U.S. Pat. No. 4,191,181; Portner U.S. Pat. No. 4,265,241; Dorman International Publication No. WO81/00209; and Fischell U.S. Pat. No. 4,373,527. Also, in my copending application Ser. No. 554,197, filed Mar. 22, 1983 now U.S. Pat. No. 4,604,090 and assigned to the same assignee as the present invention, there is disclosed a programmable pulsatile type of implantable device which employs a medication reservoir pressure stabilizing chamber operating at a pressure below body pressure so that upon failure of the pulsatile pumping unit, or the inlet valve, medication will not flow out into the body in uncontrollable and possibly harmful quantities. Such a negative pressure programmable device is particularly desirable for use with medication such as insulin which requires a wide range of infusion rates ("dynamic range") from the pumping unit to accommodate the widely varying requirements of the patient at different times of the day, and yet positively insures against an overdose of insulin in the event the device fails. This "patient fail safe" design feature is absolutely mandatory for an insulin delivery device, since an overdose of insulin can cause insulin shock which can be fatal.

While such a negative pressure programmable device will safely dispense insulin over a wide dynamic range, it is difficult to manufacture and fill the pressure stabilizing chamber at a pressure below body pressure (atmospheric), as described in my above-identified copending application. Also, care must be taken in refilling the reservoir of a negative pressure device with drug to avoid the introduction of air into the medication reservoir, and special vacuum conditioned (degassed) "pump stabilized" insulin is required, as discussed in my copending application Ser. No. 694,707 filed Jan. 24, 1985 now abandoned and assigned to the same assignee as the present invention.

On the other hand, chemotherapy drugs and most other medications are stable enough for pump usage, so a positive pressure programmable type of device, which is more easily refilled, offers the advantage of using currently available medications directly off the shelf without vacuum conditioning. The programmability feature of such a positive pressure device provides infusion rate consistency and ease of dosage rate adjustment which is not possible with the continuous flow unprogrammable medication infusion devices now on the market. However, with a programmable implantable device that uses a reservoir pressure greater than body pressure, some arrangement must be provided to prevent the excessive flow of medication into the body in the event of valve failure or the like.

A positive pressure programmable device can also be used to dispense insulin, or any other drug where overdose could be fatal, only if it can be designed to be "patient fail safe" in the event of its failure to operate. Moreover, when insulin is dispensed a further problem arises due to the fact that some diabetics cannot tolerate a complete stoppage of insulin due to failure of the device to operate while they are sleeping. If the programmable pumping unit or its electronic drive should fail to operate during the night all flow of insulin would stop and a hyperglycemic (high blood glucose) episode, leading to a potentially fatal condition known as ketoacidosis could result if the patient is especially sensitive to this condition and does not awaken to take corrective action. Accordingly, if a positive pressure programmable device is used to dispense insulin it would be desirable not only to design the device to prevent overdose in the event of failure, but also to provide a minimum basal flow of insulin in the event of failure of the programmable pumping unit or its electronic drive. It is also desirable when dispensing insulin to provide a large range of programmability since the basal and postprandial (mealtime) rates may vary widely from one patient to another. For example, one patient may require only 20 units of insulin per 24 hours while another patient may require 80 units per 24 hours.

In addition, when insulin is dispensed by a programmable device, of either the positive pressure type or the negative pressure type, there may be long periods between pump actuations when no medication is forced out of the catheter by the pump, as for example, during nighttime when a very low flow rate of medication is required. During these periods, the catheter may tend to become clogged. However, with conventional dispensing devices the patient is given no warning that the catheter is starting to clog or has, in fact, become completely plugged.

It is, therefore, an object of the present invention to provide a new and improved implantable medication infusion device wherein one or more of the above-discussed disadvantages of prior art arrangements is avoided.

It is another object of the present invention to provide a new and improved positive pressure, programmable device having a high dynamic range in which the maximum flow of medication into the body in the event of valve failure is limited to a safe value well under the maximum infusion rate of the device.

It is a further object of the present invention to provide a new and improved positive pressure, programmable device having a high dynamic range in which facilities are provided for ensuring a minimum flow of medication into the body in the event of failure of the programmable pumping unit or its electronic drive.

It is another object of the present invention to provide a new and improved positive pressure programmable device which employs a first flow restrictor between the pumping chamber and the catheter outlet to limit the flow of medication into the body to a safe value well under the maximum infusion rate of the device, in the event the inlet valve between the medication reservoir and the pumping chamber remains open or leaks excessively.

It is a further object of the present invention to provide a new and improved positive pressure programmable device which employs a second flow restrictor to provide a continuous flow of medication to the catheter outlet in the event of failure of the programmable pumping unit of the device. Preferably this second flow restrictor is an orifice type flow restrictor which substantially reduces variations in the continuous infusion rate due to body temperature and altitude changes that occur in capillary type flow restrictors.

It is another object of the present invention to provide a new and improved positive pressure programmable device for dispensing insulin wherein said second flow restrictor is connected between the reservoir and the pumping chamber and the series flow resistance of said second and first flow restrictors upon failure of said pumping unit is low enough to provide a minimum continuous basal infusion rate which flow is high enough to prevent ketoacidosis but low enough to avoid hypoglycemia during low insulin demand periods, such as exercise.

It is still another object of the present invention to provide a new and improved positive pressure programmable device for dispensing insulin wherein different ranges of minimum basal, maximum inlet valve leakage and maximum post prandial infusion rates may be provided to accommodate a wide range of patient requirements.

It is a further object of the present invention to provide a new and improved programmable device of either the positive or negative pressure type in which the operation of the device is periodically checked and an audible alarm is produced when the catheter is starting to restrict or has become completely plugged.

It is another object of the present invention to provide a new and improved programmable device of either the positive or negative pressure type, in which the size of the bolus of medication is periodically checked and an audible alarm is produced when bolus size falls below a predetermined level.

BRIEF DESCRIPTION OF THE DRAWINGS

The invention, both as to its organization and method of organization, together with further objects and advantages thereof, will best be understood by reference to the following specification taken in connection with the accompanying drawings, in which:

FIG. 3 is a fragmentary sectional view, on an enlarged scale, taken along the line 3—3 of FIG. 1;

FIG. 4 is a fragmentary sectional view, on an enlarged scale, taken along the line 4—4 of FIG. 1;

FIG. 5 is a fragmentary sectional view, on an enlarged scale, taken along the line 5—5 of FIG. 1;

FIG. 6 is a fragmentary sectional view taken along the line 6—6 of FIG. 5;

FIG. 7 is a fragmentary sectional view, on an enlarged scale, taken along the line 7—7 of FIG. 1;

FIG. 8 is a fragmentary sectional view taken along the line 8—8 of FIG. 5;

FIG. 9 is a schematic diagram of the components of the infusion device of FIG. 1;

FIG. 10 is a greatly expanded plan view of an integral filter and capillary flow restrictor unit used in the device of FIG. 1;

FIG. 11 is a sectional view taken along line 11—11 of FIG. 10.

FIG. 15 is employed;

FIG. 17 is a graph of the pressure transient of the solenoid actuated pump illustrating the manner in which incipient or actual failure due to catheter restriction or clogging may be detected in accordance with the present invention;

FIG. 18 is a graph similar to FIG. 17 but illustrating the manner in which reduced bolus size may be detected in accordance with the present invention; and FIG. 19 is a block diagram of a detection and alarm circuit which may be employed to detect either of the abnormal conditions shown in FIGS. 17 or 18.

Figure 2:
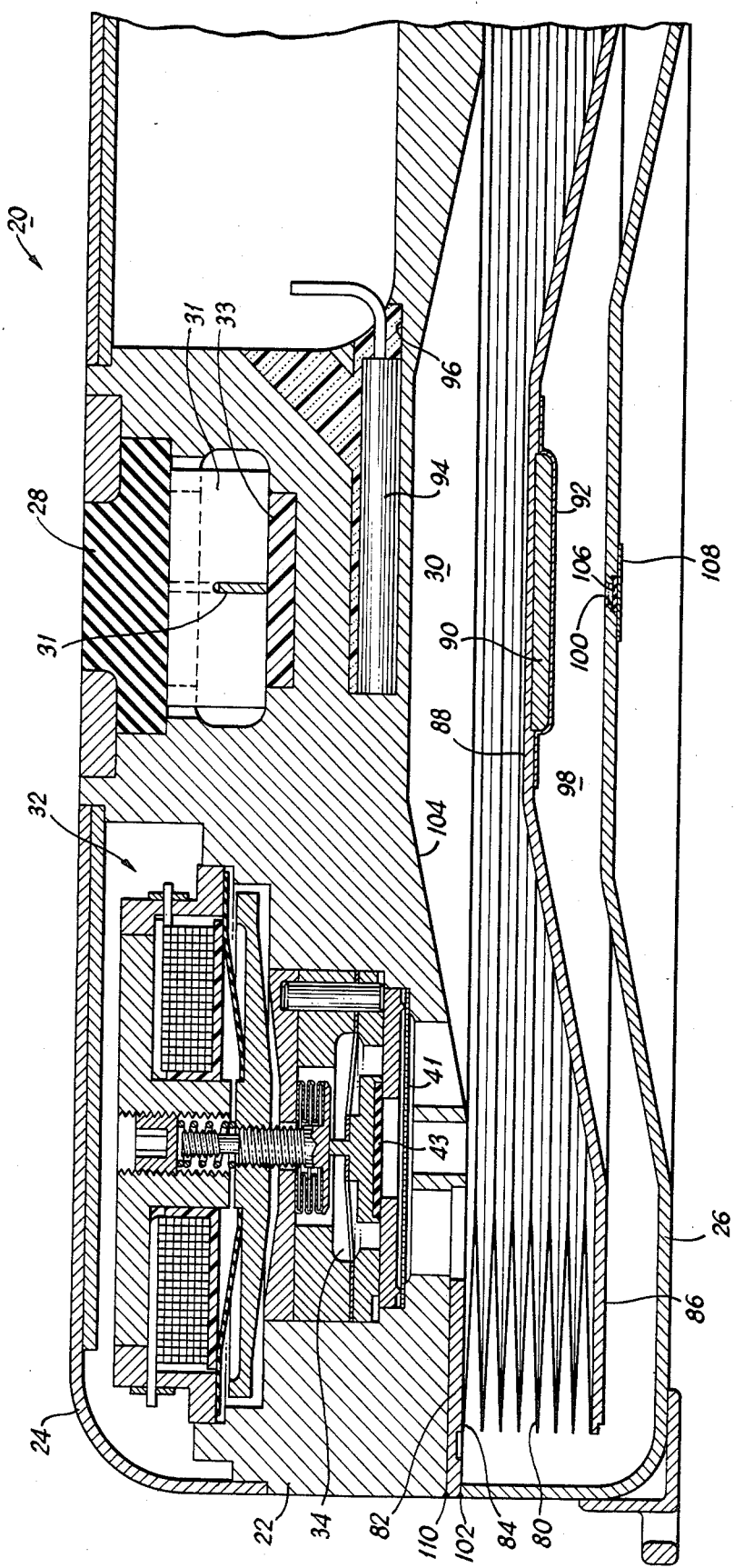
FIG. 2 is a fragmentary sectional view taken along the line 2—2 of FIG. 1.

Referring now to the drawings, the implantable medication infusion device 20 of the present invention includes a manifold 22 which is preferably made of titanium, which together with a top cover member 24 and a bottom housing 26 forms a completely sealed implantable unit which is suitable for dispensing a desired medication into the body in accordance with the fixed or variable program. More particularly, the device 20 includes a penetrable septum 28 located at the center of the device, which communicates with the medication reservoir 30 (FIG. 2) through an optional input filter 29 shown diagrammatically in FIG. 9. Medication in the reservoir 30 is supplied to a solenoid actuated pumping unit indicated generally at 32, the outlet from the pumping chamber 34 of the pumping unit 32 being supplied through the conduit 36 to a pressure transducer 38. The pressure transducer 38 senses the pressure in the pumping chamber 34 and may be employed to control the time of actuation of the pumping unit 32, as described in detail in my U.S. Pat. No. 4,486,190. In the alternative, the pressure transducer 38 may be employed to determine whether the pumping unit 32 is operating properly.

The output from the pumping unit 32 is supplied through the conduit 40 to a flow control unit 42, preferably in the form of an integral filter and flow control unit of the type described in detail in my copending application Ser. No. 697,514, filed Feb. 1, 1985 and assigned to the same assignee as the present invention. The outlet of the flow control unit 42 is supplied through a conduit 44 to a catheter unit indicated generally at 46 to which a suitable tube may be connected to supply medication from the device 20 to any desired part of the patient's body. Preferably, the catheter 46 includes a quick disconnect feature which may be changed to provide any desired orientation of the catheter tube relative to the device 20, as will be described in more detail hereinafter.

In accordance with an important feature of the present invention a second flow control unit indicated generally at 48 is mounted within the manifold 22 and is connected between the reservoir 30 and the pumping chamber 34 so that the flow control unit 48 effectively bypasses the pumping unit 32. The implantable device 30 generally, and the solenoid actuation pumping unit 32 specifically, are similar to the arrangement disclosed in my copending application Ser. No. 554,197 referred to previously, and reference may be had to said application for a detailed description of the construction and operation of the pumping unit 32. However, in accordance with an important aspect of the present invention, the medication reservoir 30 is operated at a positive pressure relative to body pressure so that a minimum basal flow of medication is provided in the event the pumping unit 32 or its electronic drive system fails. Such an arrangement insures that when insulin is being infused a minimum flow of insulin will always be provided to prevent ketoacidosis, as will be described in more detail hereinafter. Operation of the medication reservoir 30 at a positive pressure relative to body pressure has the additional advantage that the programmable infusion device 20 is more easily refilled and can use currently available medications directly off the shelf without vacuum conditioning.

The medication from the reservoir 30 is supplied through the conduit 50, a filter 52 and the conduit 54 to the center of the flow control unit 48. The output of the flow control unit 48 is supplied to an annular recess 56 in the manifold 22, this recess communicating with a passageway 58 which communicates with the passageway 49 to the inlet of the flow control unit 42. Accordingly, the auxiliary flow control unit 48, which bypasses the pumping unit 32, provides a minimum basal flow of medication from the reservoir 30 through the two flow control units 48 and 42 connected in series to the catheter 46 in the event of failure of the programmable pumping unit 32 or the electronic drive system employed to actuate the solenoid of this pumping unit.

A filter 41 is provided between the reservoir 30 and the inlet valve 43, this filter preferably being either of woven wire mesh or a porous membrane, as described in detail in my copending application Ser. No. 554,197. The filter 41 is sufficiently flexible to deflect during the pump intake stroke an amount sufficient to permit one microliter of prefiltered medication to pass into the pumping chamber 34 through the inlet valve 43, also as described in said copending application. The filter 52 may also be a woven wire screen, such as a wire mesh of double dutch twilled weave having a wire count of 325×2300 and a micron rating of 15 microns, or a porous membrane having a micron rating of from 0.22 to 5.0 microns. However, the filter 52 need not be flexible since it is not associated with the variable volume pumping chamber 34.

Figure 12:
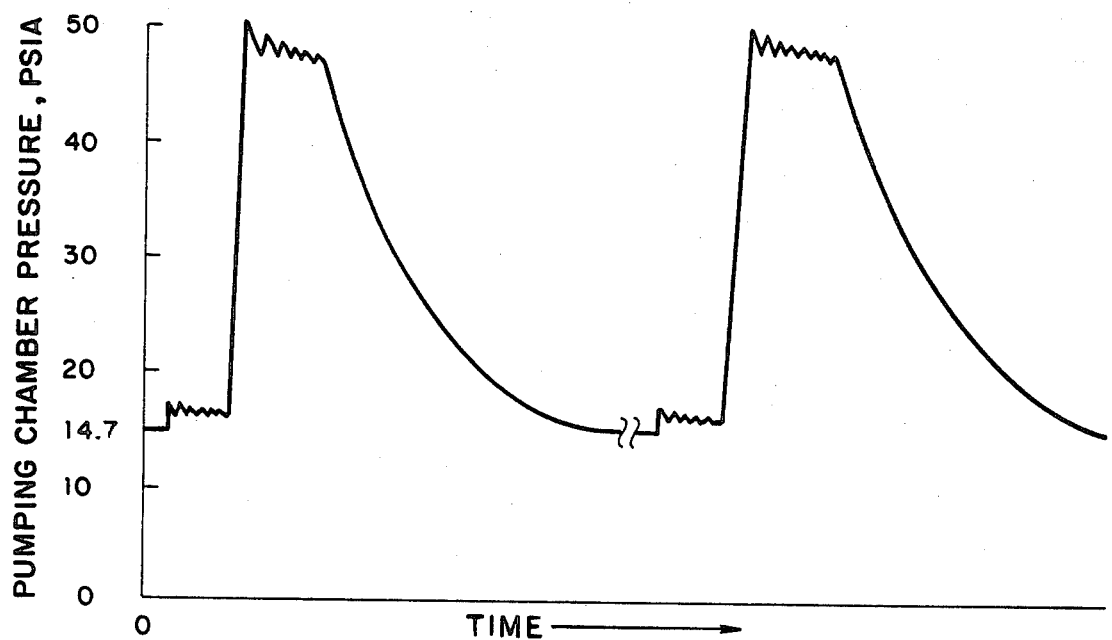
FIG. 12 is a timing diagram showing the operation of the pumping unit in a conventional or full decay mode.

While the flow control unit 42 is generally similar to the integral filter and flow control unit described in my copending application Ser. No. 697,514, in accordance with a further important aspect of the present invention the flow control unit 42 is employed to limit the flow of medication to the catheter 46 to a value which will not be harmful to the patient in the event that the inlet valve 43 (FIG. 2), which is connected between the reservoir 30 and the pumping chamber 34, leaks or fails in the open position. Since the reservoir 30 is preferably operated at a positive pressure relative to body pressure for the reasons described in detail heretofore, a failure or leakage of the valve 43 could cause an excessive flow of medication into the body. However, in accordance with the present invention, the restriction of the flow control unit 42 is made great enough to limit such flow of medication to a maximum tolerable value in the event of leakage or failure of the inlet valve 43. Such restriction is made possible in the device 20 of the present invention because of the inclusion of the solenoid operated pumping unit 32 which is operated in conjunction with the positive pressure medication reservoir 30. More particularly, during a pump output stroke the pressure within the pumping chamber 34 will rise to approximately 50 psia (as shown in FIG. 12) which is several times greater than the positive pressure in the medication reservoir 30 and is sufficient to give the desired dynamic range capability to the implantable device 20 so that the flow rate of insulin during mealtimes, for example, can be substantially increased relative to the basal insulin flow rate. For example, if the solenoid operated pumping unit 32 is actuated every ten seconds and provides one microliter of medication during each pumping stroke, a maximum medication flow rate of 0.360 milliliters per hour can be provided during mealtimes, whereas an infusion rate of only 0.11 milliliters per hour would result in the event of a failed inlet valve. If 0.11 milliliters per hour is not tolerable under a valve failure condition, then the flow control unit 42 can have more restriction but with a proportional reduction in dynamic range.

Considering now in more detail the flow control unit 42 and referring to FIGS. 10 and 11, in the arrangement of the present invention, medication is supplied to the center of the unit 42 and the outlet from the unit 42 is at the periphery thereof. More particularly, the flow control unit comprises a silicon substrate 45 and glass backing plate 57, the substrate 45 being provided with a central opening 47 which communicates with the passageway 40 in the manifold 22 through the passageway 49 (FIG. 3). Medication then passes through the inlet filter grooves 59 to the inlet of a capillary trough 51, the outlet of this capillary trough being supplied through the outlet filter grooves 53 to the outlet opening 55 in the silicon substrate 45. The opening 55 communicates with an annular recess 61 (FIG. 3) in the manifold 22 and through the passageway 44 to the catheter 46. The unit 42 is held in place by means of a cover 62 which seats on an annular spacer 64 positioned in a top opening recess 66 in the manifold 22. An O ring 68 is provided in the cover 62 and an O ring 70 is provided in the manifold 22 to seal the unit 42 and prevent flow of medication around the outside of the unit 42 from inlet to outlet.

The filter grooves 59 and 53, and the capillary groove 51 are all formed in the manner described in detail in my copending application Ser. No. 697,514 now U.S. Pat. No. 4,626,244 and reference may be had to said application for a detailed description thereof. However, as discussed heretofore, the restriction provided by the capillary groove 51 is sufficiently great to limit the medication infusion rate to a maximum tolerable value in the event of leakage or failure of the inlet valve 43. More particularly, the capillary groove 51 preferably has a cross sectional area of $5 \times 10^{-7}$ square inches and a length of 15 inches to provide such patient fail-safe restriction.

The flow control unit 48 comprises an integral filter and flow control unit which may be generally similar to the flow control unit 42. However, the size of the capillary trough provided in the flow control unit 48 is chosen so as to provide the above described minimum basal flow of medication taking into account that such flow is through the two flow control units 42, and 48 in series. For example, the minimum basal flow through the series restrictors 42 and 48 can be chosen to be 0.25 units per hour (u/hr.) of insulin which is the equivalent of 2.5 microliters of 100 u/ml strength insulin per hour. If the capillary groove of the restrictor 42 has the dimensions given in the preceding paragraph, the capillary groove of the restrictor 48 should have a cross sectional area of $8.3 \times 10^{-7}$ square inches and a length of 15 inches to provide a minimum basal flow of 0.25 u/hr. to prevent ketoacidosis. Under these condition, the flow rate in event of leakage or failure of the inlet valve 43 will be 2.5 u/hr.

The continuous minimum flow through the restrictors 42 and 48 can be supplemented by periodic boli through the pumping unit 32 to obtain the total basal flow needed by a particular diabetic. For example, if a total basal flow of 1 u/hr. is required, the pump 32 must supply 0.75 u/hr. (7.5 microliters/hour) which means the pump 32 is given 7.5 pulses/hour (assuming the pump output is one microliter for each actuation of the solenoid and 100 u/ml insulin potency is used) or one pulse every eight minutes. Diabetics normally require from 0.7 to 1.1 u/hr. but these requirements can vary over the relatively wide range of from 0.25 u/hr to 3.25 u/hr. In this connection, it will be noted that there is a loss in electro-mechanical pumping efficiency due to a small backflow of medication through restrictor 48 into the reservoir 30 during the discharge stroke of the pump 32. However, this is partly offset because a portion of the basal flow (or perhaps all of the basal flow in some patients) is provided without requiring any electrical power.

There is thus provided in accordance with an important feature of the invention, a minimum basal flow of 2.5 microliter/hr to the catheter 46 even though the solenoid operated pumping unit 32 is completely inoperative. This is important when the device 20 is employed to dispense insulin due to the fact that some diabetics cannot tolerate a complete stoppage of insulin while they are sleeping and may experience a hyperglycemic (high blood glucose) episode, leading to a potentially fatal condition known as ketoacidosis. The provision of such a minimum basal flow of medication by the flow control unit 48 is also important to reduce catheter clogging due to blood thrombosis or clotting (Intravenous delivery) and tissue growth (Intraperitoneal delivery) even if the pump 32 is operating properly. In this connection, it should be noted that with programmable pump devices there may be long periods between pump actuations when no medication is forced out of the catheter by the pump, as for example, during nighttime when a very low flow rate of medication is desired. During these periods, the catheter may tend to become clogged. However, with the arrangement of the present invention, a continuous although very low velocity flow is provided by the flow control unit 48 during periods between actuations of the solenoid operated pump 32 to reduce the incidence of catheter clogging.

Figure 13:
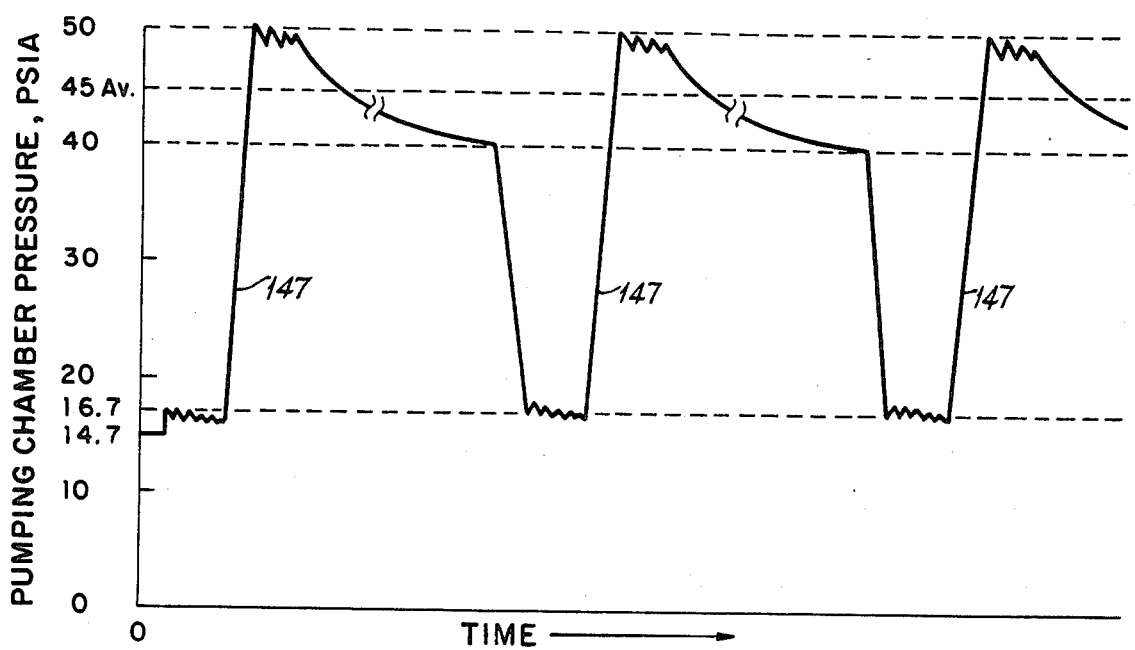
FIG. 13 is a timing diagram showing the operation of the pumping unit in a fast pulsing mode.

When the pumping unit 32 is operated in the conventional or "full pressure decay" mode, as shown in FIG. 12, the amount of time required to force a given bolus of one microliter through the restrictor limits the maximum post prandial rate which can be achieved to a relatively low value. However, in accordance with a further feature of the present invention, the maximum post prandial flow rate may be substantially increased by operating the pumping unit 32 in a so-called "fast pulsing mode", as shown in FIG. 13. Referring to this figure, in the fast pulsing mode the solenoid is actuated so rapidly that the pressure in the pumping diameter does not have a chance to decay down to the catheter outlet pressure but instead remains at a relatively high value. Thus, in FIG. 13, the solenoid is pulsed as soon as the pressure in the pumping chamber falls to 40 psia so that an average pressure of approximately 45 psia is maintained in the pumping chamber. In this connection, it should be pointed out that in FIG. 13 the solenoid intake stroke pulse periods 147 are of very short duration (10 milliseconds) whereas the solenoid exhaust stroke decay of pressure from 50 psia to 40 psia is of relatively long duration (2 seconds). When the pumping unit 32 is operated in the fast pulsing mode, i.e., at an average pressure in the pumping chamber of 45 psia, a maximum post prandial flow rate of 15 u/hr. may be achieved with the restrictors 42 and 48 of the dimensions given above by actuating the pump every 2 seconds. Thus, in the fast pulsing mode of FIG. 13, the pump is given 1800 pulses/hour whereas in the basal flow mode of FIG. 12 the pump is given 7.5 pulses/hour.

Figure 1:
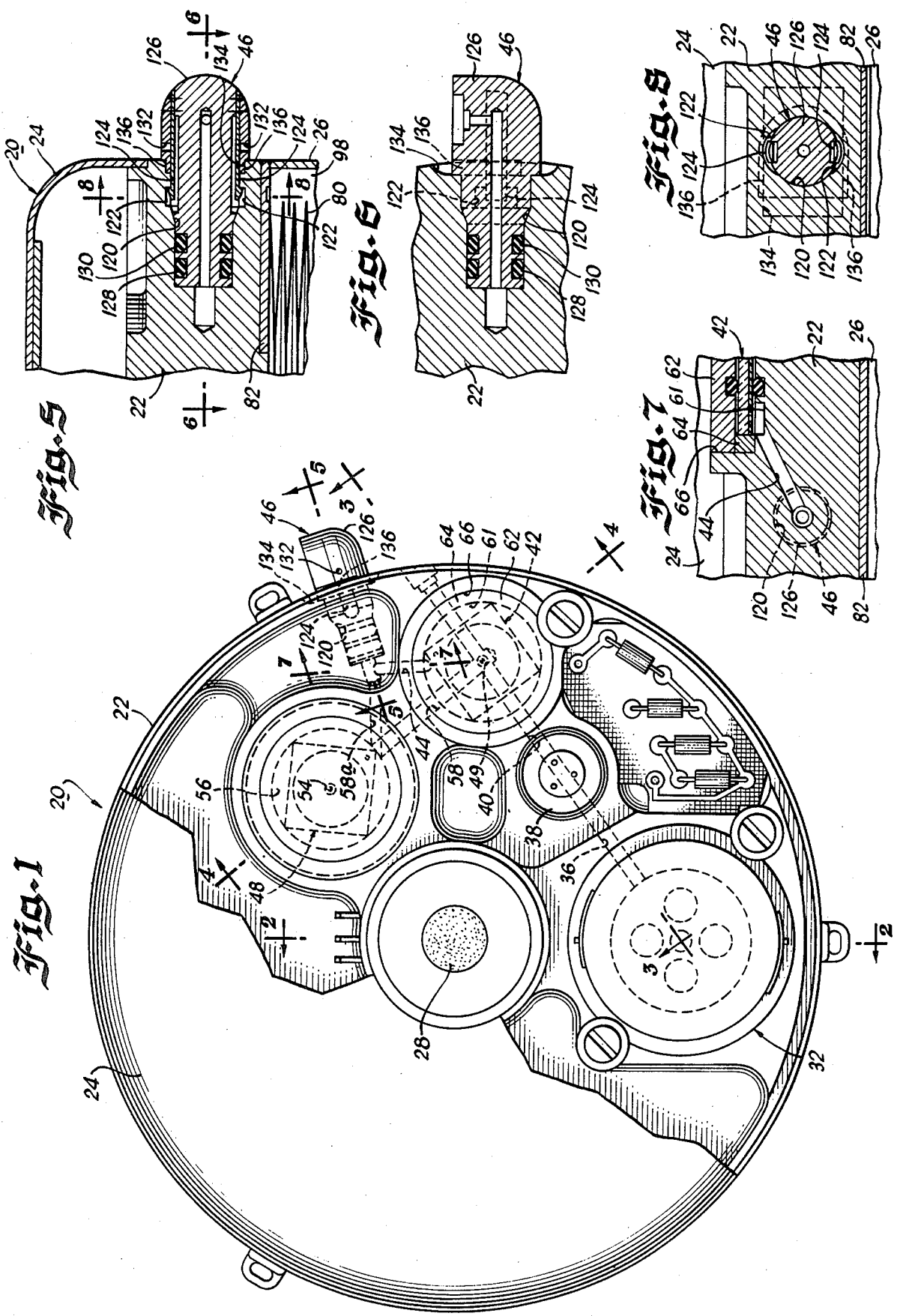
FIG. 1 is a plan view of an implantable medication infusion device embodying features of the present invention.

While the auxiliary flow restrictor 48 has been described thus far as being connected in series with the flow restrictor 42, it is also possible to connect the auxiliary flow restrictor between the reservoir 30 and the catheter 46 so that the auxiliary flow restrictor 48 bypasses both the pumping unit 32 and the flow restrictor 42. More particularly, as shown in FIGS. 1 and 9, the outlet of the flow restrictor 48 may be connected through the passageway 58a to the catheter 46 and the passageway 58 eliminated. When the passageway 58a is used, the system has a slightly better volumetric efficiency. However, when the passageway 58 is used the leaky valve infusion rate is slightly lower than when the passageway 58a is used.

While the flow control units 42 and 48 have been described as being of the capillary type, it should be pointed out that these units, particularly the unit 48 which establishes a minimum basal flow to prevent ketoacidosis, may preferably be orifice type restrictors of the type described in detail in my copending application Ser. No. 697,514 now U.S. Pat. No. 4,626,244. Such orifice type restrictors substantially reduce variations in the continuous basal flow rate due to body temperature and altitude changes, as described in detail in my copending application Ser. No. 697,514 now U.S. Pat. No. 4,626,244.

From the above description, it will be seen that the medication infusion device of the present invention provides fail-safe protection for two failure modes, i.e. loss of pumping action by the pumping unit 32, and leakage or failure of the inlet valve 32. However, as discussed generally heretofore, the amount of insulin required over a 24 hour period varies widely from one diabetic patient to the next. Thus, one patient who requires 80 u/24 hours may be able to withstand safely a much higher valve leakage rate than a patient who requires only 20 u/24 hours. In accordance with a further aspect of the present invention, patients may be divided into three categories, Group A which require from 20 to 40 u/24 hours, Group B which require from 40 to 60 u/24 hours, and Group C which require from 60 to 80 u/24 hours. These three groups of patients may be accommodated in two different ways.

Figure 14:
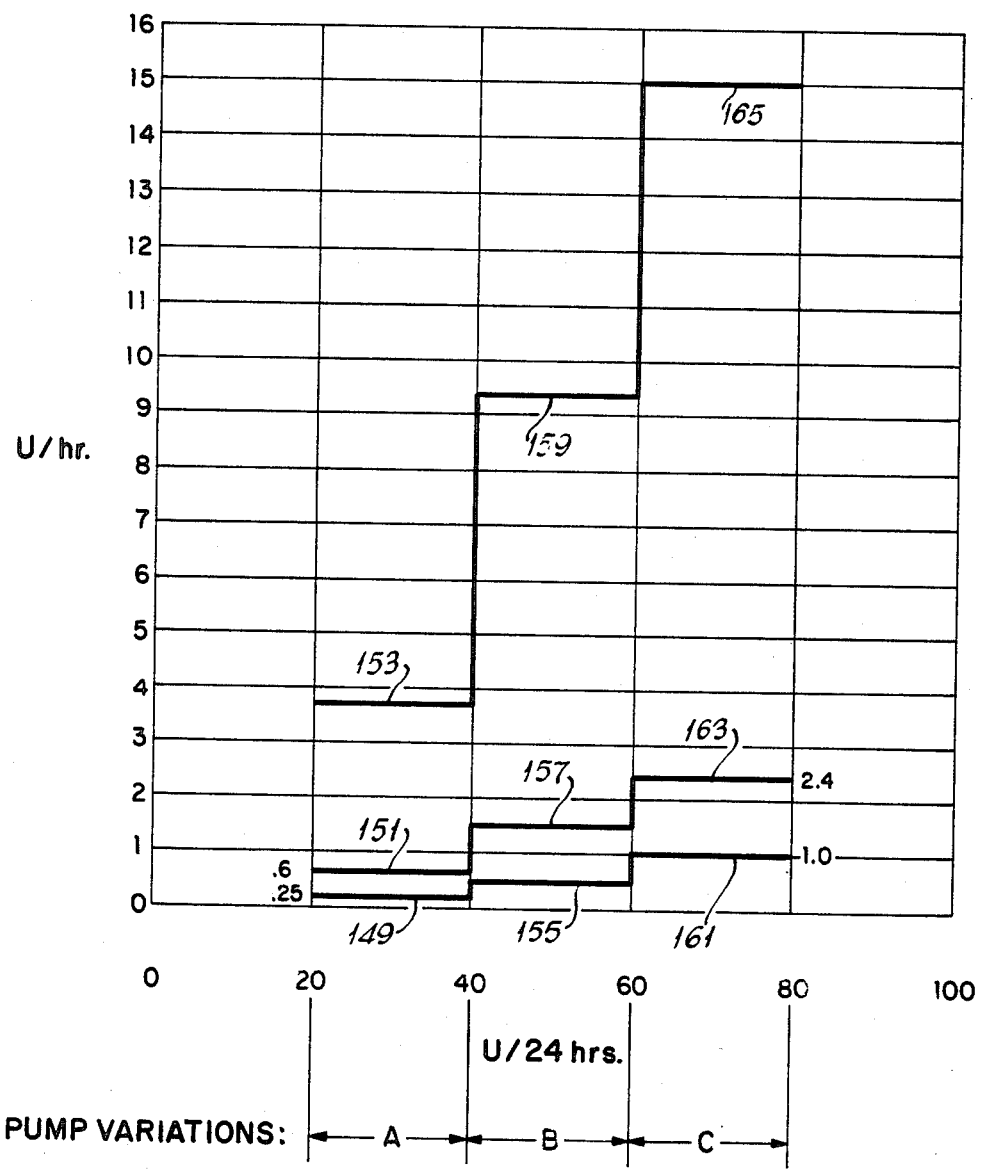
FIG. 14 is a graph illustrating the manner in which the medication infusion device of the present invention can be calibrated for use with patients having different insulin requirements.

First, as shown in FIG. 14, the three groups of patients may use different pumps which are flow calibrated at the factory to take into account the different requirements of each group, each of these pumps using 400 u/ml strength insulin. Thus, as shown in FIG. 14 the Group A infusion device will have a minimum basal flow rate of 0.25 u/hr. to prevent ketoacidosis, as shown by the line 149, an inlet valve leakage (failure) flow rate of 0.6 u/hr. as shown by the line 151 and a maximum post prandial flow rate of 3.7 u/hr., as shown by the line 153. The Group B device will have a minimum basal flow rate of 0.5 u/hr., as shown by the line 155, an inlet valve leakage rate of 1.5 u/hr., as shown by the line 159, and a maximum post prandial flow rate of 9.4 u/hr., as shown by the line 59. The Group C device will have a minimum basal flow rate of 1.0 u/hr, as shown by the line 161, an inlet valve leakage rate of 2.4 u/hr., as shown by the line 163, and a maximum post prandial flow rate of 15 u/hr., as shown by the line 165.

Figure 15:
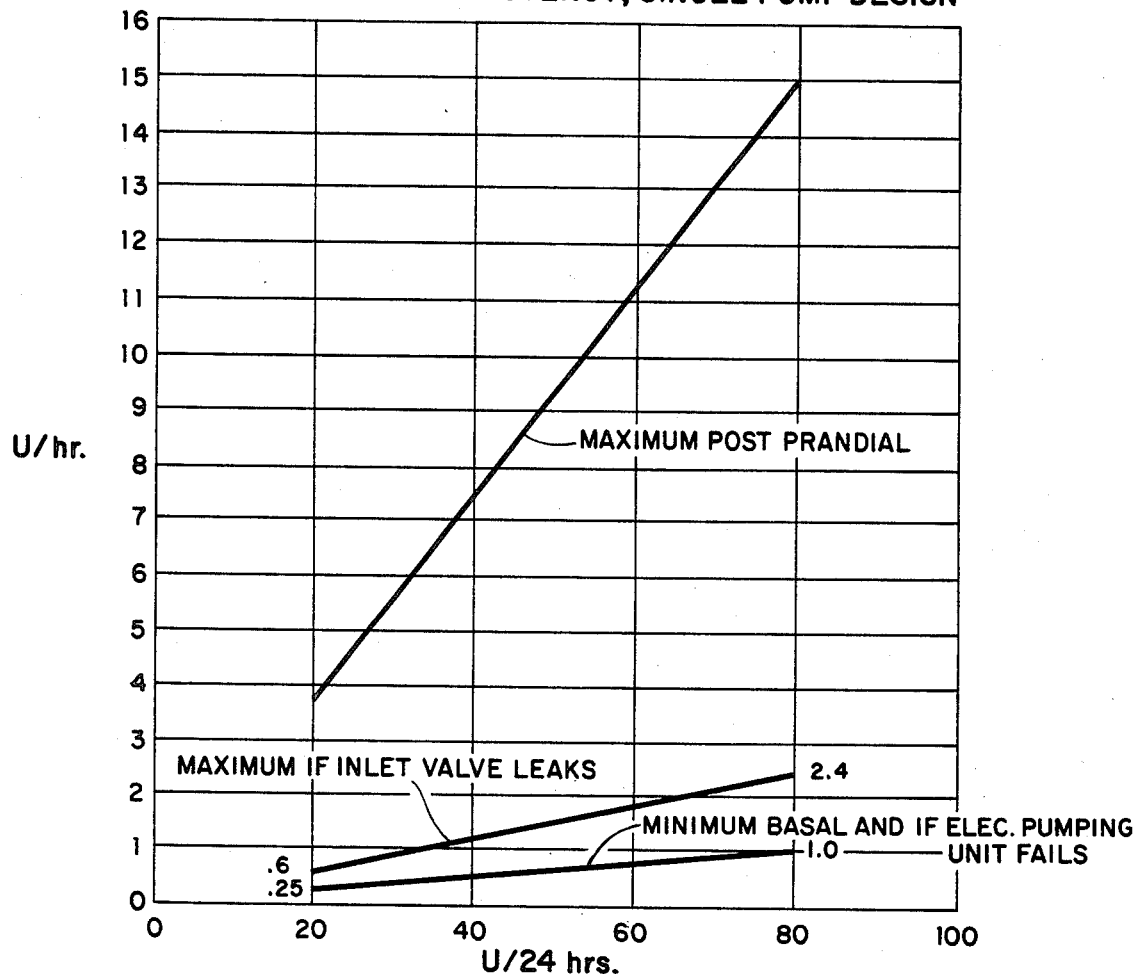
FIG. 15 is a graph illustrating how the medication infusion device of the present invention may accommodate patients with different insulin requirements by variation of the insulin potency in the reservoir of the device.

The second way of accommodating these three groups of patients is to use a single pump design and vary the potency of the insulin used with each group, as shown in FIG. 15. With this approach, the different flow rates of the pump do not have to be changed for different groups of patients but instead the insulin potency is varied to meet each group's requirements. For example, 400 u/ml strength insulin can be used for 80 u/24 hr. patients with proportional dilution for patients who require less insulin per day—down to 100 u/ml for patients that need 20 u/24 hr. It will be noted from FIG. 15 that the inlet valve leakage rate and minimum basal flow rate vary correspondingly in this second method of accommodating the wide range of patient daily insulin needs.

Figure 16:
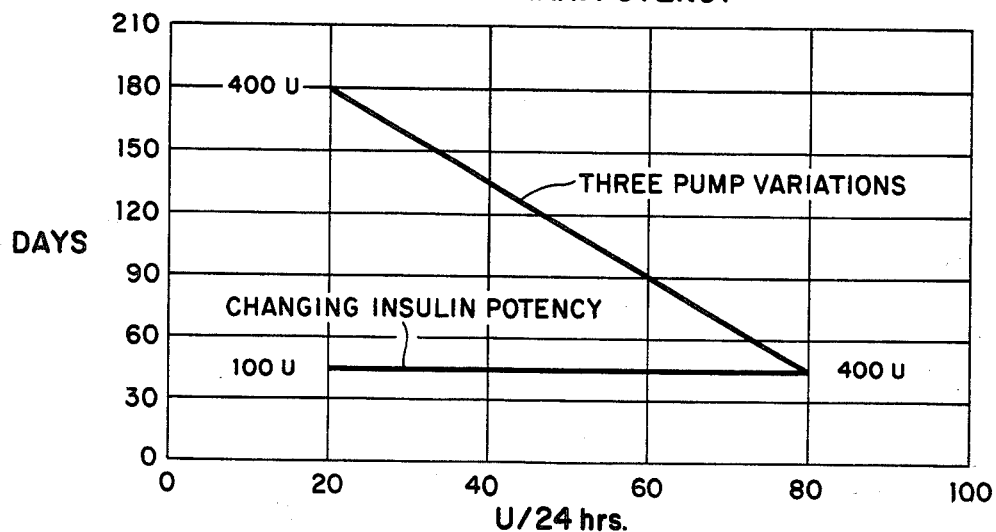
FIG. 16 is a graph of variations in the refill interval of the infusion device of the present invention when the arrangement of either FIG. 14

In FIG. 16 there is shown the refill interval for the two different approaches of FIG. 14 and FIG. 15. Referring to this figure, it can be seen that the arrangement of FIG. 15, in which insulin potency is varied according to the patients needs, has a fixed refill period of 45 days. On the other hand, the three pumps having different flow restrictors for different maximum flow rates, all of which use 400 u insulin, will have different refill periods, the shortest period being for the pump for Group C having a maximum post prandial flow of 15 u/hr.

As discussed generally heretofore, when a programmable solenoid actuated pump of either the positive or negative pressure type is employed, there may be long periods of time between pump actuations during which the catheter may tend to become clogged. While the very low velocity flow provided by the flow control unit 48 tends to prevent catheter clogging in a dispensing device of the positive pressure type, it would be desirable to provide an arrangement whereby incipient catheter clogging or incipient pump failure can be detected and an audible alarm given to the patient when such condition occurs. In FIGS. 17 to 19, a further embodiment of the invention is shown wherein such abnormal conditions may be detected and indicated to the patient. It should be emphasized that the incipient failure and failure warnings provided in the embodiment of FIGS. 17-19 can be employed in a programmable device of either the positive or negative pressure type and independently of the use of the bypass flow control unit 48. For example, the detection system of FIGS. 17-19 may be employed in a negative pressure programmable device of the type, shown in my copending application Ser. No. 554,197 now U.S. Pat. No. 4,604,090.

Referring now to FIG. 17, the pressure pulse or transient which is developed by the pumping unit 32 each time the solenoid thereof is actuated is detected by the pressure transducer 38. As can be seen from this figure, this pressure transient normally rises to approximately 50 psia when the solenoid is actuated and then decays back to ambient pressure (14.7 psia) in about 8 seconds, as shown by the pressure wave labelled NORMAL. However, if the catheter is restricted this pressure wave will decay more slowly, as indicated by the wave labelled RESTRICTED CATHETER. It should be emphasized that with a restricted catheter the pressure may still decay to ambient so that the patient will still receive a full bolus (usually one microliter) but receives it over a longer time period.

In accordance with the detection system of FIGS. 17 and 19 the pressure within the pumping chamber is measured immediately prior to the instant of solenoid actuation and again approximately 8 seconds after the solenoid is actuated, as shown by point A in FIG. 17. If this pressure is below 20 psia an indication is provided that the catheter is unclogged and the pressure wave is decaying in a normal manner. However, if the pressure wave is still above 20 psia 8 seconds after the solenoid is actuated an indication is provided that the catheter is clogged or restricted. Furthermore, this indication is an early warning of the incipient or impending failure of the programmable device when the catheter becomes completely plugged up. Such an incipient failure warning could not be obtained by measuring the amount of insulin dispensed because a full bolus may be dispensed over a longer period of time even though the catheter is partially clogged.

If the pressure measured immediately prior to the instant of solenoid actuation is greater than 20 psia, then the pressure is not decaying back to ambient body pressure prior to actuating the solenoid. In this event the preceding pulse bolus is less than the normal one microliter because the catheter is clogged more severely than in the preceding example, where the catheter is clogged but not enough to reduce the bolus to a value less than the normal one microliter. As in the foregoing incipient failure case, the patient is alerted by audible alarm of this failure condition.

FIG. 19 shows a suitable detection and alarm arrangement which may be employed in the incipient detection system of FIG. 17. Referring to this figure, the output of the pressure transducer is amplified by a factor of 100 in the instrument amplifier 71 and then supplied to a sample and hold circuit 72. In order to sample the pressure wave at point A of FIG. 17, a timer circuit 73 is employed which first resets the sample and hold circuit 72 at its output No. 1 and then supplies a pulse to actuate the pump solenoid drive circuit 74 at its output No. 2. Approximately 80 milliseconds later the timer 73 develops a pulse at its output No. 3 which is supplied to the sample and hold circuit 72 so that a signal is developed in the output thereof which is proportional to the pressure in the pumping chamber at point A in FIG. 17. This output signal is supplied to one input of a comparator 75 to the other input of which a reference voltage proportional to a pressure of 20 psia in the pumping chamber. If the output of the sample and hold circuit 72 is greater than this reference voltage a signal is then supplied by the comparator 75 to a suitable audible alarm device 76 positioned within the implanted device 24 to provide a direct alarm to the patient of the incipient failure due to catheter clogging. The timer circuit 73 may be initiated several times each 24 hours by means of a pulse from the programmed electronics portion of the implanted device, preferably when the device is operating in a post-prandial discrete bolus mode. In this connection, it should be understood that if the catheter has become completely plugged at the time the sample and hold circuit 72 is energized the pressure within the pumping chamber will not decay at all but will remain at a high level considerably above 20 psia. This condition will, of course, also be detected by the circuit of FIG. 19 and an alarm given.

The pressure in the pumping chamber may also be checked at point B in FIG. 17, i.e., just prior to actuation of the solenoid pump. With this alternative arrangement, the timer 73 simply resets the sample and hold circuit 72 and then sets it just prior to actuation of the solenoid drive circuit 74, i.e., without an 8 second delay. When the pressure is sampled at point B and is found to be above 20 psia, an abnormal condition due to catheter clogging or plugging (that has reduced the pump bolus to less than its normal one microliter) is indicated to the patient, as described in detail heretofore in connection with FIG. 19.

In FIG. 19, an arrangement is shown for detecting when the size of the bolus is reduced and hence provide an indication of incipient or actual pump failure. Referring to this figure, if the pumping system has failed due to the introduction of air into the pumping chamber or because of an electronic or mechanical failure, the pressure wave or transient developed in the pumping chamber may be much smaller than normal, as indicated by the wave labelled LOW OUTPUT in FIG. 18. If the pressure in the pumping chamber is sampled at point C approximately 15 milliseconds after solenoid actuation and is found to be less than 40 psia an indication is provided that the solenoid pump is not operating properly. To detect the pressure at point C of FIG. 18 the detection system of FIG. 19 is employed. However, the timer 73 is arranged to energize the sample and hold circuit 72 approximately 15 milliseconds after the solenoid is actuated. Also, the reference voltage for the comparator 75 is set to a level proportional to 40 psia and the comparator is arranged to provide an output to the alarm circuit 76 if the output from the sample and hold circuit is less than 40 psia. In other respects the detection system of FIG. 19 operates in the manner described in detail heretofore in connection with FIG. 17.

While the implantable device 20 is generally similar to the arrangement described in my copending application Ser. No. 554,197, this device is different from said arrangement in certain respects. More particularly, the septum 28 is held in compression by means of a pair of crossed strut members 31 which engage the underside of the septum 28 and prevent it from bulging downwardly when a needle is inserted through the septum 28 during a refill operation. The struts 31 are provided with interlocking notches to form a cruciform structure which also holds the needle stop 33 in place within the manifold 22. The struts 31 extend at right angles to each other and are relatively thin so that they do not interfere with the insertion of a needle through the septum 28. The struts 31 keep the elastomer septum 28 in a compressive state so that when a needle is withdrawn the hole in the septum is reliably sealed by the compressive forces in the septum 28.

In order to provide a relatively large medication reservoir 30, which may hold on the order of 25 milliliters of medication, an annular bellows 80 (FIG. 2) is secured at its upper end to a mounting plate 82 by means of the weld joint 84 and is secured at its bottom end to the outer periphery of a movable plate 86 which forms the bottom wall portion of the bellows. The plate 86 is provided with an elevated central portion 88 and a permanent magnet 90 is held against the underside of the central portion 88 by means of the retaining plate 92. A Hall effect transducer 94 is inserted through an opening 96 in the manifold 22 so that it is positioned above the permanent magnet 90. The Hall effect transducer 94 and the permanent magnet cooperate to provide an indication of the volume of medication in the chamber 30, as described in detail in my copending application, Ser. No. 554,197 now U.S. Pat. No. 4,604,090.

The space between the cover 26 and the plate 86 and bellows 80 provides a pressure stabilizing chamber 98 which can be filled with a fluid which through a change of state establishes a substantially constant pressure on the medication within the reservoir 30 despite changes in the volume of medication within this reservoir and changes in temperature and pressure within the body. Since the pressure within the stabilizing chamber 98 is positive relative to body pressure, the chamber 98 is preferably filled in accordance with the procedure described in detail in my copending application Ser. No. 697,514, now U.S. Pat. No. 4,626,244, which relates to a positive pressure non-programmable device. To facilitate this filling operation the plate 82 is welded to the upper edge of the cover 26 by means of the weld 102 to provide a separate subassembly, this subassembly being associated with a member simulating the wall 104 of the manifold 22 during the filling operation, all as described in my copending application Ser. No. 697,514 now U.S. Pat. No. 4,626,244. A plug 106 is then resistance welded into the opening 100 while the unit is submerged in expelled fluorocarbon fluid to prevent the introduction of air into the chamber 98 and a redundant seal is provided by TIG, laser or electron beam welding a thin piece of titanium 108 over the plug 106, all as described in my copending application Ser. No. 697,514 now U.S. Pat. No. 4,626,244. The fluid within the chamber 98 may comprise either FC-87 or FC-88 perfluorocarbon fluid (vapor pressure of 17.5 psia at 98.6° F.) or Freon 11 fluorocarbon fluid which has a vapor pressure equal to 23 psia at 98.6° F., as described in my copending application Ser. No. 697,514 now U.S. Pat. No. 4,626,244. After the pressure stabilizing chamber 98 has been filled, the bellows subassembly is welded to the manifold 22 by means of the weld 110. Alternately, the bellows subassembly is added to the manifold 22 by means of the weld 110 before the pressure stabilizing chamber 98 is filled with fluid.

In accordance with a further aspect of the present invention, the catheter 46 is provided with a quick disconnect feature whereby the catheter 46 may be readily removed from the device 20 without requiring the doctor to loosen and retighten set screws which are quite tiny and hard to unscrew. Thus, referring to FIGS. 5, 6 and 8, the manifold 22 is provided with a catheter outlet port 120 and a pair of opposed outwardly directed recesses 122 are formed in the wall of the port 120 which are adapted to receive the hooked end portions of a pair of flexible arms 124. The arms 124 are secured to a connector body 126 which is insertable into the port 120 and contains the O rings 128 and 130 positioned in suitable grooves in the end of the connector body 126 in order to seal the catheter 46 to the manifold 22. The outer ends of the spring arms 124 are secured to the connector body 126 by any suitable means such as spot welding and a pair of opposed openings 132 are provided in the connector body 126 through which a suitable tool may be inserted to depress the spring arms 124 and release the hooked end portions thereof from the recesses 122.

In order to prevent the connector body 126 from rotating relative to the manifold 22, the manifold 22 is provided with a milled slot 134 in the periphery thereof and the connector body 126 is provided with milled flats 136 in the periphery thereof. The flats 136 engage the sides of the slot 134 when the connector body 126 is fully inserted into the port 120 and prevent the body 126 from rotating. However, in accordance with a further feature of the invention, the catheter 46 may readily be removed from the device 20 and reinserted with a 180° change in orientation by depressing the spring arms 124 while the catheter 46 is pulled out of the outlet port 120 after which the catheter 46 is rotated 180° and reinserted into the port 120 until the hooked end portion of the spring arms 124 extend outwardly into the recesses 122 and hold the connector body 126 securely in the new orientation. Accordingly, the catheter 46 may be oriented in a desired direction to conform to the requirement of a particular implantation.

While there has been described what is at present considered to be the preferred embodiments of the invention, it will be understood that various modifications may be made therein which are within the true spirit and scope of the invention.

What is claimed as new and desired to be secured by Letters Patent of the United States is:

1. In an implantable medication infusion device, the combination of, a medication reservoir having a movable wall portion, a pressure stabilizing chamber in communication with said movable wall portion and filled with a fluid having a pressure which is greater than the pressure of the body in which said device is implanted, a solenoid operated pulsatile pumping unit having an inlet communicating with said reservoir through an inlet valve; and a flow restrictor positioned between said pumping unit and a catheter outlet, said flow restrictor permitting; and continuous flow of medication to said catheter outlet at a safe value rate in the event said inlet valve remains open.

2. The combination of claim 1, wherein said pulsatile pumping unit provides a predetermined maximum flow rate through said flow restrictor, and said continuous flow of medication to said catheter when said inlet valve remains open is limited to approximately one-third of said predetermined maximum flow rate by said flow restrictor.

3. The combination of claim 2, wherein said predetermined maximum flow rate is approximately 0.36 milliliters per hour.

4. The combination of claim 3, wherein said continuous flow rate is approximately 0.11 milliliters per hour.

5. In an implantable medication infusion device, the combination of, a medication reservoir having a movable wall portion, a pressure stabilizing chamber in communication with said movable wall portion and filled with a fluid having a pressure which is greater than the pressure of the body in which said device is implanted, a solenoid operated pulsatile pumping unit having an inlet communicating with said reservoir through an inlet valve; a first flow restrictor positioned between said pumping unit and a catheter outlet, and a second flow restrictor connected across said inlet valve, said second flow restrictor providing a predetermined continuous minimum flow of medication from said reservoir through said second and first flow restrictors to said catheter outlet during periods when said pumping unit is not operating.

6. The combination of claim 5, wherein said second flow restrictor comprises a large number of series connected orifices which collectively provide said predetermined continuous minimum flow.

7. The combination of claim 5, wherein said first flow restrictor also limits the continuous flow of medication from said reservoir to said catheter to a predetermined value in the event said inlet valve does not function properly, said predetermined value being greater than said continuous minimum flow of said second flow restrictor but substantially less than the maximum flow rate when said pumping unit is operating.

8. The combination of claim 5, wherein said predetermined continuous flow provided by said second flow restrictor is in the order of 2.5 microliters per hour.

9. The combination of claim 1, wherein the continuous flow of medication through said flow restrictor is in the order of 0.11 milliliter per hour.

10. The combination of claim 7, wherein said predetermined value is in the order of 0.11 milliliters per hour.

11. The combination of claim 7, wherein said maximum flow rate when said pumping unit is operating is in the order of 0.36 milliliters per hour.

12. In an implantable medication infusion device, the combination of a medication reservoir, means for supplying medication from said reservoir to a catheter outlet port, said catheter outlet port including an inwardly extending shoulder, and a quick detachable outlet port connector having a connector body adapted to fit into said catheter outlet port in fluid sealing relation thereto and having a pair of spring arms provided with outwardly extending lug portions on the free ends thereof which are adapted to engage said shoulder and hold said connector securely within said outlet port, said spring arms being inwardly deflectable to disengage said lug portions from said shoulder, thereby to permit said connector to be quickly removed from said outlet port.

13. The combination of claim 12, wherein said connector body includes a pair of rigid arms contiguous to said pair of spring arms, each of said rigid arms having an aperture therein through which said spring arms may be deflected.

14. The combination of claim 12, wherein said connector body includes at least one groove within which is positioned an O ring to provide said fluid sealing relation between said connector body and said catheter outlet port.

15. The combination of claim 12, which includes means for interlocking said connector within said catheter outlet port in a plurality of orientations relative to said outlet port.

16. The combination of claim 12, which includes means carried by said outlet port connector for securing a catheter thereto.

17. In an implantable medication infusion device, the combination of, a medication reservoir having a movable wall portion, a pressure stabilizing chamber in communication with said movable wall portion and filled with a fluid having a pressure which is greater than the pressure of the body in which said device is implanted, a solenoid operated pulsatile pumping unit having an inlet communicating with said reservoir through an inlet valve; a first flow restrictor positioned between said pumping unit and a catheter outlet, and a second flow restrictor connected between said reservoir and said catheter outlet, said second flow restrictor providing a predetermined continuous minimum flow of medication from said reservoir to said catheter outlet during periods when said pumping unit is not operating.

18. The combination of claim 17, wherein said second flow restrictor comprises a large number of series connected orifices which collectively provide said predetermined continuous minimum flow.

19. The combination of claim 17, wherein said first flow restrictor also limits the continuous flow of medication from said reservoir to said catheter to a predetermined value in the event said inlet valve does not function properly, said predetermined value being greater than said continuous minimum flow of said second flow restrictor but substantially less than the maximum flow rate when said pumping unit is operating.

20. The combination of claim 17, wherein said predetermined continuous flow provided by said second flow restrictor is in the order of 2.5 microliters per hour.

* * * * *